United States Patent
Le Berre et al.

(10) Patent No.: US 9,803,173 B2
(45) Date of Patent: Oct. 31, 2017

(54) DEVICE FOR GUIDING CELL MIGRATION AND GUIDING METHOD IMPLEMENTING SUCH A DEVICE

(71) Applicants: Institut Curie, Paris (FR); Centre National de la Recherche Scientifique—CNRS, Paris (FR); Societe de Developpement et de Recherche Industrielle, Chenove (FR)

(72) Inventors: Mael Le Berre, Paris (FR); Matthieu Piel, Paris (FR); Yong Chen, Paris (FR); Yanjun Liu, Courbevoie (FR)

(73) Assignees: INSTITUT CURIE, Paris (FR); CENTRE NATIONAL DE LA RECHERCHE SCIENTIFIQUE—CNRS, Paris (FR); SOCIETE DE DEVELOPPEMENT ET DE RECHERCHE INDUSTRIELLE, Chenove (FR)

( * ) Notice: Subject to any disclaimer, the term of this patent is extended or adjusted under 35 U.S.C. 154(b) by 102 days.

(21) Appl. No.: 14/345,517

(22) PCT Filed: Sep. 17, 2012

(86) PCT No.: PCT/FR2012/052073
§ 371 (c)(1),
(2) Date: Mar. 18, 2014

(87) PCT Pub. No.: WO2013/041800
PCT Pub. Date: Mar. 28, 2013

(65) Prior Publication Data
US 2015/0004692 A1 Jan. 1, 2015

(30) Foreign Application Priority Data
Sep. 19, 2011 (FR) ...................................... 11 58316

(51) Int. Cl.
*C12N 5/00* (2006.01)
*C12N 5/077* (2010.01)
(Continued)

(52) U.S. Cl.
CPC .......... *C12N 5/0068* (2013.01); *B29C 39/026* (2013.01); *B29C 39/42* (2013.01);
(Continued)

(58) Field of Classification Search
CPC C12N 5/0068; C12N 5/0656; C12N 2533/30; C12N 2535/00; C12N 2533/52;
(Continued)

(56) References Cited

U.S. PATENT DOCUMENTS 5,330,911 A * 7/1994 Hubbell ................ A61L 17/145
435/402
2006/0097361 A1* 5/2006 Tanaka ................ B01D 69/06
257/643
2009/0248145 A1 10/2009 Chan et al.

FOREIGN PATENT DOCUMENTS

WO WO 2009158631 A1 * 12/2009 ........... B29C 39/026

OTHER PUBLICATIONS

Marmaras et al. Topography-mediated apical guidance in epidermal wound healing. Soft Matter, May 2012, 6922-6930.*
(Continued)

*Primary Examiner* — Taeyoon Kim
(74) *Attorney, Agent, or Firm* — McAndrews, Held & Malloy, Ltd.

(57) ABSTRACT

The subject matter of the present invention is a device for guiding cell migration comprising a substrate having a textured surface intended to be brought into contact with cells, said textured surface having an anisotropic three-dimensional structure consisting of a network of projections inclined relative to the normal to the plane formed by said textured structure, in the direction imparted by said anisotropic structure.

(Continued)

A. Simple adhesive structures
– cells not confined

B. Non-adhesive structures –
cells confined

C. Cells confined on a "soft" support surface

D. Cells confined *in vivo*

The invention also concerns, according to another aspect, a method for guiding cell migration including the bringing into contact of cells with a substrate having a textured surface and an anisotropic three-dimensional structure, said structure consisting of projections inclined as previously described.

The device or method according to the invention can in particular be applied in the fields of dermatology, implantology and tissue engineering.

25 Claims, 4 Drawing Sheets (51) Int. Cl.
  *B29C 39/42* (2006.01)
  *B29C 39/02* (2006.01)
  *B29K 67/00* (2006.01)
  *B29K 105/00* (2006.01)
  *G03F 7/00* (2006.01)

(52) U.S. Cl.
  CPC ........ *G03F 7/0035* (2013.01); *B29K 2067/04* (2013.01); *B29K 2105/0085* (2013.01); *B29K 2883/00* (2013.01); *C12N 5/0656* (2013.01); *C12N 2533/30* (2013.01); *C12N 2533/32* (2013.01); *C12N 2533/52* (2013.01); *C12N 2535/00* (2013.01)

(58) Field of Classification Search
  CPC ... C12N 2533/32; B29C 39/026; B29C 39/42; G03F 7/0035; B29K 2067/04; B29K 2105/0085; B29K 2883/00
  See application file for complete search history.

(56) References Cited

OTHER PUBLICATIONS

Park et al. Cell Motility and Local Viscoelasticity of Fibroblasts. Biophysical Journal vol. 89 Dec. 2005 4330-4342.*

French Search Report and Opinion in FR1158316 dated Aug. 3, 2012.

Goher Mahmud et al., "Directing cell motions on micropatterned ratchets," Nature Physics, 5(8):606-612 (2009) XP055034675.

Hwa Seng Khoo et al., "Engineering the 3D architecture and hydrophobicity of methyltrichlorosilane nanostructures," Nanotechnology, 19(34):345603 (2008) XP020144505.

International Search Report in PCT/FR2012/052073 dated Nov. 28, 2012.

Se Yon Hwang et al., "Adhesion Assays of Endothelial Cells on Nanopatterned Surfaces within a Microfluidic Channel," Analytical Chemistry, 82(7):3016-3022 (2010) XP055034676.

* cited by examiner

Figure 1

Inclined projections  PDMS support  Glass coverslip
surface

Figure 2

A. Simple adhesive structures – cells not confined

B. Non-adhesive structures – cells confined

C. Cells confined on a "soft" support surface

D. Cells confined *in vivo*

DEVICE FOR GUIDING CELL MIGRATION AND GUIDING METHOD IMPLEMENTING SUCH A DEVICE

The present application is filed pursuant to 35 U.S.C. 371 as a U.S. National Phase application of International Patent Application No. PCT/FR2012/052073, which was filed Sep. 17, 2012, claiming the benefit of priority to French Patent Application No. 1158316, which was filed on Sep. 19, 2011. The entire text of the aforementioned applications is incorporated herein by reference in its entirety.

The subject of the present invention is a device for guiding cell migration, comprising a substrate having a textured surface which has an anisotropic three-dimensional structure intended to be put into contact with cells.

Cell migration is essential for many physiological processes, such as organogenesis and wound healing. In their natural environment, the direction and the speed of migration of cells are guided by numerous signals which may be chemical (chemokines) or physical (microenvironment).

In vitro, these phenomena can be reproduced or diverted to impose a direction of migration on the cells using, for example, chemoattractants or electric fields, or else by modulating the mechanical environment of the cell.

Document EP-A-1199354 describes, for example, the formation of a cell pattern on a surface by chemical control of the cell migration. Indeed, in document EP-A-1199354, the surface is treated so as to exhibit a pre-pattern consisting of compounds which promote cell growth, and other compounds which do not promote cell growth. The culturing of the cells is then initiated on this pre-pattern. However, the effectiveness of the control of the cell migration by this type of system depends mainly on the choice of the chemical compounds which promote or prevent cell growth according to the nature of the cells cultured.

Document US 2007/0009572 describes, for its part, a method for preparing a microtextured or nanotextured biodegradable film comprising channels, the width of which can range from 10 to 160 µm, on which muscle cells are deposited. The tests carried out show that the muscle cells align with one another along the channels, and that their morphology becomes modified so as to take on an elongated shape. The purpose of this method is not to cause the cells to migrate in a preferred direction, but just to promote their alignment with one another so as to obtain an even cell stacking.

Document US 2009/02481445 also describes a method for guiding the orientation of cells according to a three-dimensional structure using a surface comprising a microchannel or a series of microchannels parallel to one another, the width of which is greater than that of the cells so that the cells can enter therein, and the cross section of which is arbitrary. As for the previous document, the purpose of this method is not to cause the cells to migrate in a preferred direction, but just to promote their alignment with one another.

Mahmud et al. (Nature Physics 2009, 4, pp. 606) propose adhesive patterns in ratchet form to guide cell migration. The effect observed is based on a contrast of adhesion between the adhesive parts of the channels and the non-adhesive parts of a substrate such that, when the quality of the contrast between the adhesive and non-adhesive parts degrades over time, the guiding of cell migration is no longer observed. In addition, the adhesion on the linear channels or the channels which are in ratchet form makes it possible to maintain the cells only on these adhesive patterns, i.e. on a single dimension in space, and does not, for example, allow the organization of a tissue on a surface in two dimensions. Finally, the patterns described by Mahmud et al. are always projections that are perpendicular to the plane formed by the surface conveying the cells.

These methods which make it possible to divert the natural phenomena of cell migration can also find applications in vivo.

Document US2009/0093879 provides in particular an implant which has micrometric or nanometric three-dimensional patterns on the surface. These patterns make it possible in particular to control the adhesion of microorganisms or of fibroblasts at the surface of the implant when the latter is implanted in a living being, thus improving the healing of injuries.

This document US2009/0093879 suggests that the surface microstructures or nanostructures can guide the cells responsible for the healing, thus making it possible for them to become organized in an ordered manner at the surface of the implant.

As it happens, such a control of cell migration along a given direction could also have applications in the medical field other than the forced organization of cells around an implant, such as the directed migration of cells at the surface of a wound or the production of artificial organs by tissue engineering.

There is therefore a need for new devices which make it possible to guide cells in their migration along a chosen direction, the effectiveness of which does not depend on the motile cell type under consideration, which are simple to use, not very invasive to tissues and robust over time. For the purpose of the present application, the expression "guiding cell migration" is intended to mean that the cells are made to migrate preferentially in one direction rather than in all the other directions. In other words, the guiding of the migration breaks the symmetry of migration according to the direction under consideration. The "guiding" of migration differs from the "orienting" of cell migration where the cells preferentially migrate in two opposite directions without one of these directions being favored over the other.

An object of the present application is therefore to provide a device for guiding cell migration, comprising a substrate having a textured surface intended to be brought into contact with cells, said textured surface having an anisotropic three-dimensional structure consisting of a network of projections inclined relative to the normal to the plane formed by said textured surface, in the direction imparted by said anisotropic structure.

Contrary to the prior art documents describing channels or microchannels restricting alignment of the cells, the present invention makes it possible to guide cells according to a direction of anisotropy, thus forming a network in the plane compatible with the organization of a tissue according to a given surface.

According to a second aspect, a subject of the invention is also a method for guiding cell migration, comprising bringing the cells into contact with a substrate having a textured surface which has an anisotropic three-dimensional structure, said structure consisting of inclined projections as previously described.

Finally, according to another aspect, a subject of the invention is a kit for guiding cell migration, comprising a substrate having a textured surface as previously described, which has an anisotropic three-dimensional structure consisting of a network of projections inclined relative to the normal to the plane formed by said textured surface, in the direction imparted by said anisotropic structure, and a support surface on which cells are intended to be conveyed.

The device or the method according to the invention can in particular be applied in the fields of dermatology, implantology and tissue engineering.

For the purpose of the present application, the term "anisotropic structure" or "structure with anisotropic geometry" is intended to mean a structure of which the geometry has a direction of anisotropy which is determined according to a given axis.

The direction of anisotropy of the anisotropic structure is in particular, in the context of the present invention, the direction of the cell migration.

The device according to the invention uses a substrate having a textured surface, the three-dimensional structure of which consists of a network of inclined projections.

DESCRIPTION OF THE FIGURES

FIG. 3A): simple adhesive structures for guiding the cells in one direction.

FIG. 3B): the confinement of the cells between the textured surface and the support surface in a space of approximately 5 μm.

FIG. 3C): the application of the textured surface on a soft substrate of gel type.

FIG. 3D): the application of the textured surface on a living tissue.

FIG. 4A) illustrates a glass plate on which a layer of chromium coated with a layer of photosensitive resin is deposited.

FIGS. 4(B) and (C) illustrate the formation of the patterns on the photosensitive layer via a photolithographic process and its transfer into the layer of chromium by etching.

FIG. 4(D) illustrates the application of a layer of resin on the patterns formed.

FIG. 4(E) illustrates the UV irradiation of the layer of resin.

FIG. 4(F) illustrates the inclined projections formed following the UV irradiation.

FIG. 4(G) illustrates the consecutive deposit of a layer of PDMS silicone.

FIG. 4(H) illustrates the negative PDMS mold thus formed.

FIG. 4(I) illustrates the application of a layer of the material constituting the textured surface according to the invention on the negative PDMS mold.

FIG. 4(J) illustrates the three-dimensional surface thus formed.

SUBSTRATE

In the context of the present application, the technical effect of guiding cell migration is obtained by means of the particular textured surface as previously described, which has an anisotropic three-dimensional structure consisting of a network of projections inclined relative to the normal to the plane formed by said textured surface, in the direction imparted by said anisotropic structure, when this textured surface is brought into contact with cells.

The substrate having a textured surface, in particular a microtextured or nanotextured surface, of the device according to the invention may be adhesive or non-adhesive.

The choice of an adhesive substrate can in particular make it possible to further improve the technical effect of guiding cell migration already obtained by virtue of the device using the specific surface according to the invention.

The adhesive materials that may be suitable for the substrate according to the invention can in particular be hydrophilic or hydrophobic, while being, where appropriate, treated with a cell adhesion promoter, and in particular chosen from:

biocompatible plastics (for example polystyrene (PS) commonly used in cell culture, silicone polymers, for instance polydimethylsiloxane (PDMS), in particular used in Lab-on-a-chip devices, gels of block copolymers, for instance styrene-ethylene/butylene-styrene (SEBS), used for the manufacture of dressings, or polylactic and glycolic acids (PLGA, PLA: hydrophilic) which are biodegradable and can be used for implants or as artificial tissue supports). Some of these plastics can advantageously be activated by oxygen plasma so as to increase their hydrophilicity or to promote cell adhesion;

ceramics, generally hydrophilic ceramics, such as metal oxides, or nitrides, for instance glass ($SiO_2$), silicon nitride ($Si_3N_4$), titanium dioxide ($TiO_2$) or others. These materials are used in cell culture, in Lab-on-a-chip devices and in implantology. These materials can advantageously be activated by oxygen plasma so as to increase their hydrophilicity and to promote cell adhesion;

inert materials such as gold, platinum, palladium or metals of which the oxidized or nitrided surface is stable, for instance chromium or titanium, which are used for implants. Advantageously, the metals may be treated with molecules of the thiol family so as to increase or reduce their cell adhesion capacity.

It is also possible to promote cell adhesion by chemically treating the support material. Use may then be made of:

charged polymers (polyelectrolytes) which adsorb strongly by electrostatic interaction on oxidized surfaces (naturally as for oxides or artificially by activating the surfaces using an oxygen plasma); for example, poly-L-lysine (PLL) or polyornithine (PORN); or cell adhesion proteins (integrins) or extracellular matrix proteins (fibronectin, laminin, collagen) or peptides which mimic these proteins, for instance the RGD (arginyl glycyl aspartic acid) motif.

It is also possible, in the context of the present invention, to modulate the adhesion of the substrate so as to optimize the motility of the cells. Indeed, the level of adhesion of the cells on a substrate can be modulated by treating this adhesive substrate with a ratiometric mixture of adhesive molecules and non-adhesive molecules. For example, a mixture of PLL-PEG and of PLL-PEG-RGD or a mixture of PLL-PEG and of fibronectin can be used.

According to one preferred embodiment, the substrate having a textured surface is a non-adhesive substrate, i.e. a substrate on which the cells cannot adhere, such that they can be removed without damaging the cells. These non-adhesive substrates are also called anti-fouling substrates.

The non-adhesive nature of the substrate corresponds to a low protein adsorption capacity of said substrate and also a low cell adhesion capacity, which generally makes it possible to limit inflammatory reactions.

The non-adhesive materials which may be suitable for the substrate having a textured surface according to the invention can in particular be superhydrophobic materials—as is the case with fluoropolymers (for example polytetrafluoroethylene (PTFE))—or gels, for instance polyacrylamide (PAM) or polyethylene glycol diacrylate (PEGDA).

Alternatively, the non-adhesive substrate may consist of a material made non-adhesive by chemical treatment.

The chemical treatments which enable the substrate to be made non-adhesive can in particular be the grafting onto the substrate of a monomolecular gel layer, for example of polyethylene glycol (PEG) type, for example a PEG silanized on the oxides or thiolated on the metals or conjugated with a polyelectrolyte so as to give it the capacity to adsorb on the substrate in a long-lasting manner by electrostatic interaction, as is the case with the grafting of polylysine-PEG (PLL-PEG).

Preferably, the non-adhesive material is a fluoropolymer or a material made non-adhesive by chemical treatment, such as the grafting of molecules, for example of polyethylene glycol (PEG).

TEXTURED SURFACE

The textured surface of the device according to the invention has an anisotropic three-dimensional structure consisting of a network of inclined projections.

For the purpose of the present application, the term "network" of inclined projections is intended to mean that the inclined projections are arranged periodically on the textured surface so as to produce a regular repeating pattern.

The direction of inclination of the projections makes it possible in particular to impose a direction of lower friction, thus determining the preferential direction of movement of the cells. According to one particular embodiment, in order to enhance the friction, the network of projections exhibits a spacing, defined as the distance between two projections, which is less than the size of the cells, such that the cell is always in contact with at least two projections, preferably less than 20 µm, so as to prevent the cells from circulating randomly between the projections.

In the context of the invention, the textured surface has a size which is greater than the size of the cells.

Preferably, the spacing of the network of projections is between 0.1 and 15 µm, more preferably between 5 and 10 µm and more preferentially about 5 µm.

In the context of the invention, the projections of the network of the anisotropic three-dimensional structure constituting the textured surface are inclined relative to the normal to the plane formed by said textured surface, in the direction imparted by said anisotropic structure.

In particular, these projections preferably have an angle of inclination of less than or equal to 45° relative to the normal to the plane formed by the textured surface, and more preferably between 10° and 45°.

The projections are preferably of nanometric size, i.e. their height, measured from the substrate of the textured surface, is about one nanometer, in particular between 100 nm and 20 µm, so as to limit the indentation and to avoid piercing of the cell under the pressure of the projections.

In particular, the projections preferably have an aspect ratio, corresponding to the ratio of the height to the diameter of the projections, of between 0.5 and 20, preferably between 2 and 10.

Advantageously, this aspect ratio can be used to adjust the stiffness of the substrate perceived by the cells by using the fact that the higher the aspect ratio of the pillars, the less stiff the projections, and therefore the more easily they will be distorted under the effect of the forces applied by the cells.

For example, micropillars or nanopillars molded in a standard PDMS substrate, with a stiffness of 2 MPa, will make it possible to obtain stiffnesses ranging from 1.7 kPa for an aspect ratio of 6.25 to 61 kPa for an aspect ratio of 1.9 (Thesis by S. Ghassemi, Columbia University, 2011, pp. 38 (http://academiccommons.columbia.edu/catalog/ac:131397)).

As it happens, the stiffness of the projections makes it possible to induce a certain phenotype, a certain differentiation or the proliferation of the cells in contact with the substrate, while at the same time preserving the desired cell-guiding property according to the present application. Indeed, it has been shown that certain cells, when they develop on stiffer substrates, have a tendency to differentiate into bone cells, whereas these same cells, when they develop in more flexible substrates, have a tendency to differentiate into neuronal cells.

Consequently, it may be advantageous, in the context of the present application, to adjust the aspect ratio of the projections of the textured surface according to the invention (in particular when the cells are conveyed on this surface) so as to modify the phenotype, the differentiation or the proliferation of said cells.

The inclined projections may be in any geometrical shape, and in particular in the shape of cylinders, cones, pyramids, lamellae, or flakes of substantially triangular, semielliptical or semicircular shape.

When the projections are in the shape of lamellae, their cross section may be rectangular or in the shape of a parallelogram, the cross section being defined by a plane normal to the axis of said lamella.

According to one preferred embodiment, the inclined projections are in the shape of cylinders which can in particular have a spherical or ovoid cross section, the cross section being defined by a plane normal to the axis of said cylinder.

For the purpose of the present application, the cross section of the projections, whatever its shape, falls within a circle of predetermined diameter, defined as being the diameter of said projections.

When the diameter of the projections is not constant (for example when the projections are conical), the diameter is measured for a cross section located halfway up the projections.

The inclined projections preferably have a diameter of between 10 nm and 10 µm, preferably between 0.5 and 3 µm.

According to one particular embodiment, the area occupied by the inclined projections, arranged periodically on the textured surface, represents from 5% to 50% of the textured surface, and preferably about 5% of the textured surface.

Such anisotropic structures consisting of a network of inclined projections can, for example, be obtained by photolithography or by nanoimprint lithography, optionally followed by a step of anisotropic dry etching such as reactive-ion etching (RIE) including plasma torch systems (inductively coupled plasma, ICP) or DRIE (deep reactive-ion etching), by inclining the sample during the photolithography or during the etching so as to obtain the inclination of the structures.

PRODUCTION OF THE TEXTURED SURFACE

The textured surface of the device according to the invention, which has an anisotropic three-dimensional structure consisting of a network of inclined projections, can be prepared by any method known to those skilled in the art.

However, it is to the applicant's credit to have developed a novel method for preparing surfaces of this type.

The inclined projections can in fact be produced by casting a silicone polymer (PDMS) or by molding a poly (lactic-co-glycolic acid) (PLGA) copolymer on a silicone (PDMS) mold.

In the context of the invention, the inclined projections, when they are used for guiding cells by confinement, can preferably be made of a silicone polymer (PDMS), the surface of which is made non-adhesive.

Figure 4:
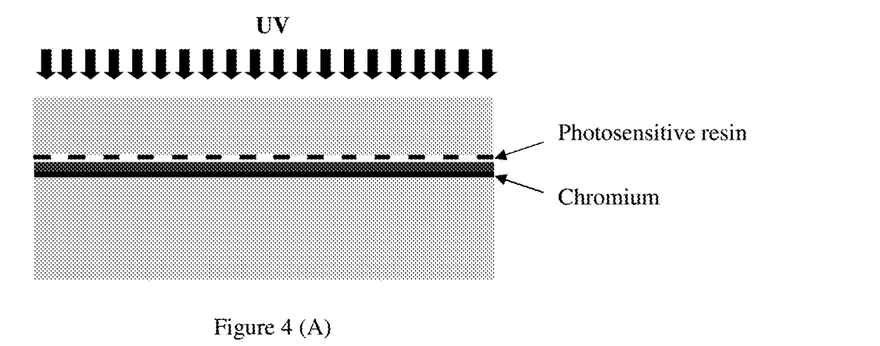
FIG. 4 illustrates the various steps of the process for preparing the textured surface according to the invention.

According to another particular aspect of the invention, the inclined projections, when they are used for guiding cells without confinement, can preferably be produced by molding a poly(lactic-co-glycolic acid) (PLGA) copolymer on a silicone (PDMS) mold as illustrated in FIG. 4.

Thus, according to one particular aspect, a subject of the invention is a process for preparing a textured surface which has an anisotropic three-dimensional structure consisting of a network of projections inclined relative to the normal to the plane formed by said textured surface, in the direction imparted by said anisotropic structure, comprising:
  i. the preparation of silicone molds constituting negative copies of said three-dimensional structure, in particular by self-aligned optical lithography,
  ii. the molding of the material constituting said three-dimensional structure,
  iii. the detachment of the silicone mold.

In particular, silicone (PDMS) molds can be prepared by self-aligned optical lithography, comprising in particular the following steps:
  i. the depositing of a layer of photosensitive resin on an optical mask,
  ii. the irradiation of said layer of resin through the optical mask using a light source, with an incident angle (corresponding to the angle formed by the incident ray and the normal to the plane formed by the mask), said incident angle conditioning the angle of inclination of the pillars of the anisotropic three-dimensional structure,
  iii. optionally, the covering of said three-dimensional surface of resin with an anti-fouling material,
  iv. the casting of a layer of PDMS on said three-dimensional surface of resin so as to obtain said silicone (PDMS) molds,
  v. after polymerization, detachment of the resulting PDMS mold (FIG. 4(H)).

The optical mask used in step i. can be a transparent substrate normally used for optical masks, for instance a glass plate, on which are formed patterns constituting the mask made of a light-absorbing metallic material, for example chromium. These masks are conventional for photolithography and are commercially available or can be produced by methods known to those skilled in the art.

Those skilled in the art can, for example, produce an optical mask by depositing a light-absorbing metallic layer (in particular chromium) on a transparent substrate such as a glass plate and by forming patterns (for example a matrix of holes) on said metallic layer, for example by etching with a chromium-etching solution such as ChromeEtch, sold by MicroChem.

For this, patterns are produced by scanning of a laser beam focused on a layer of photosensitive resin deposited on the transparent substrate (glass plate) covered beforehand with a layer of chromium. After revealing of the resin, these patterns are transferred onto the layer of chromium by dipping the glass substrate in a bath of ChromeEtch. To finish, the patterns of resin having served as a mask are removed using an appropriate solvent.

An unused mask of PR-AZ1518 Cr type (glass plate covered with a thin layer of chromium and with a layer of resin), sold by MicroChem, can, for example, be used for producing optical masks.

In step i, the thickness of the layer of resin applied is in particular chosen according to the desired height of the pillars. The resin is, for example, an SU-8 3000 epoxy resin sold by the company MicroChem.

Once the resin has been crosslinked in step ii, the part of the resin which has not been irradiated can preferably be removed, using an appropriate solvent.

The angle chosen for the irradiation in step ii defines the angle of inclination of the projections relative to the normal to the plane formed by said textured surface (FIG. 4(E)). Since the light is refracted in the transparent substrate used, the angle of the pillars is not always exactly the angle of the light; this depends on the nature of the material constituting the substrate. Those skilled in the art will therefore adjust the incident angle according to the substrate used so as to obtain the desired inclination of the pillars.

The angle chosen for the irradiation in step ii can in particular be less than 90°, preferably less than 45° and more preferentially between 10° and 45°.

The anti-fouling material optionally added in step iii can, for example, be trimethylchlorosilane (TMCS).

Finally, on the basis of the resulting PDMS molds, the anisotropic three-dimensional surface as claimed in the invention is produced by molding of a material (PDMS or PLGA) constituting said three-dimensional structure according to the invention, for example by casting a silicone polymer on the silicone mold placed under vacuum beforehand, or by thermal molding in the case of a poly(lactic-co-glycolic acid) (PLGA) copolymer.

After curing of the material constituting the three-dimensional surface, the PDMS mold is separated from the sample of three-dimensional surface thus having a network of projections inclined relative to the normal to the plane formed by said textured surface, in the direction imparted by said anisotropic structure (FIG. 4(J)).

When the anisotropic three-dimensional surface according to the invention is produced by thermal molding of a PLGA copolymer, said molding is carried out at a temperature of between 80 and 100° C. (preferably from 60 to 90° C., and more preferentially approximately 90° C.), and at a pressure of between 60 and 120 bar (preferably between 100 and 120 bar, and more preferentially approximately 120 bar), for approximately 10 minutes (FIG. 4(I)). After cooling and reduction of the pressure to reach atmospheric pressure, the PDMS mold is separated from the sample of three-dimensional surface.

The height, the diameter and the angle of inclination of the projections can thus be modulated by those skilled in the art by adjusting various parameters of the process.

SUPPORT SURFACE

In the context of the device according to the invention, the cells of which the migration is controlled are conveyed on a substrate referred to as "support surface".

The support surface on which the cells lie can be the textured surface previously described, or an artificial surface such as a cell culture surface (for example a gel), a glass coverslip, the inside of a microfluidic channel, or a surface of the natural environment of said cells, such as the surface of a living tissue or the surface of a wound.

According to one particular embodiment of the invention, the cells can be guided by confining them between their support surface and said textured surface.

Indeed, the confinement of the cells makes it possible to reinforce the guiding of the cells, in particular when the substrate on which the cells are conveyed is non-adhesive.

In this embodiment, the distance between said support surface and said textured surface is between 0 and 10 µm, preferably between 3 and 6 µm such that the thickness of the cell after confinement is at least between 3 and 6 µm so as to allow its migration.

When the support on which the cells are conveyed is "soft", i.e. has a stiffness of less than approximately 20 kPa, in particular of between 100 Pa and 20 kPa, preferably between 500 Pa and 10 kPa, it is not necessary for it to have additional protuberances since the surface is sufficiently "soft" to allow the cells to not be crushed by the nanotextured substrate, the cells defining their confinement space by deforming the support surface.

These "soft" supports are of low-stiffness gel or cell layer type. The gels used may be gels of artificial origin, such as polyacrylamide (PAM) or polyethylene glycol diacrylate (PEGDA), or else gels of natural origin, such as collagen, matrigel or hyaluronic acid (HA). The stiffness of these gels can be adjusted through their composition and through the conditions for crosslinking them.

Conversely, when the support on which the cells are conveyed has a stiffness of greater than approximately 20 kPa, it is desirable, in the context of the present invention, for said support to have additional protuberances so as not to impair the cells.

The support surface and/or said textured surface may comprise one or more additional protuberances which make it possible to control the distance between the two said surfaces. The height of these protuberances is measured relative to the surface on which they are placed.

The additional protuberances may in particular be in the form of pillars with a diameter of between 100 and 500 µm, and a height of between 1 and 10 µm, preferably between 3 and 6 µm, and in any event with a height such that the thickness of the cell after confinement is at least between 3 and 6 µm when the support has a stiffness of greater than approximately 20 kPa.

METHOD FOR GUIDING CELL MIGRATION

A subject of the invention is also a method for guiding cell migration, comprising bringing the cells into contact with a substrate having a textured surface which has an anisotropic three-dimensional structure, said structure consisting of projections inclined relative to the normal to the plane formed by said textured surface, in the direction imparted by said anisotropic structure.

In this method, the textured surface is as previously described.

The cells are also conveyed on a support surface as previously described, such that the cells can be confined between said textured surface and said support surface.

A subject of the invention is also a device comprising a substrate having a textured surface intended to be brought into contact with cells, said textured surface having an anisotropic three-dimensional structure consisting of a network of projections inclined relative to the normal to the plane formed by said textured surface, in the direction imparted by said anisotropic structure, for use in a method for guiding cell migration.

APPLICATIONS

The device according to the invention can in particular have numerous applications in guiding cell migration in vivo or in vitro.

The term "guiding in vitro" is intended to mean guiding the migration of cells in culture in an entirely artificial medium.

The cells can, for example, be cultured on an artificial support surface, such as a cell culture surface (for example a gel), the textured surface then being applied on the support surface in order to confine the cells.

In another embodiment, the textured surface can be integrated on one of the faces of a microfluidic channel in order to guide the migration of the cells in said microfluidic channel.

The textured surfaces of the device according to the invention can be used either for studying the biological and physical mechanisms of migration and proliferation of cells in culture, or for performing cell sorting by separating the cells according to their migration characteristics.

Alternatively, the device according to the invention may make it possible to guide cells on two-dimensional or three-dimensional supports at least partially covered with a textured guiding surface for producing artificial organs (tissue engineering).

The device according to the invention may be applied in any field where it is necessary to guide cells artificially and independently of their chemotactic behavior.

The term "guiding in vivo" is intended to mean guiding cell proliferation and migration in a living being, for example in human beings.

In this case, the support surface consists of the natural physiological support of the cells, on which the textured surface is applied.

According to one preferred embodiment of guiding in vivo, the textured surface can be used to guide the cells present at the surface of a wound so as to promote the distribution of the cells on the wound. The device is then a dressing which has microstructures or nanostructures at its surface.

According to another embodiment of guiding in vivo, the textured surface can be used to guide the cells around a prosthesis so as to promote the distribution of the cells around the prosthesis.

According to yet another embodiment of guiding in vivo, the textured surface can be used to guide the cells around an internal film or dressing placed inside the body of a living being so as to promote the distribution of the cells in or around an organ.

The device according to the invention can in particular be in the form of a dressing, an implant, a prosthesis, an artificial-tissue support, a microfluidic channel, or a Lab-on-a-chip device integrating channels, and preferably said device is a dressing.

EXAMPLE

The cell-migration-guiding effect of the device according to the invention was established on cell cultures of normal human skin fibroblasts (NHDFs) in the laboratory.

NHDF cell cultures were covered with a silicone (polydimethylsiloxane PDMS) surface covered with a square network of inclined cylinders. The network of inclined cylinders has the following properties: spacing of 4 µm, diameter of 1.5 µm, height of 5 µm, and with an inclination of 40° relative to the normal to the plane formed by said surface (see FIG. 2).

The network of inclined cylinders was prepared by casting a PDMS silicone polymer on a silicone (PDMS) mold, as illustrated in FIG. 4.

The silicone (PDMS) molds were prepared using a mold produced by self-aligned optical lithography.

For this, an optical mask consisting of a glass plate covered with a thin layer of chromium and with a layer of AZ1518 resin, sold by MicroChem, referenced as PR-AZ1518 Cr, is used as basic substrate.

Patterns, in this case a matrix of holes, were made on said layer of photosensitive resin by scanning of a laser beam focused on said photosensitive layer (FIG. 4(B)) followed by a resin development step.

These patterns are then transferred onto the layer of chromium, which is light-absorbing, by wet etching (ChromeEtch) and the resin patterns are removed with isopropanol (FIG. 4(C)).

A layer of thick SU-8 3005 epoxy resin sold by the company MicroChem, about 5 µm thick, was then deposited onto the glass plate comprising the previously defined patterns (FIG. 4(D)).

The glass plate comprising said layer of resin was then turned over so as to be UV-irradiated on the glass plate side, with an incident angle of approximately 70° such that the angle of inclination of the cylinders relative to the normal to the plane formed by said textured surface is 40° (FIG. 4(E)).

After revealing of the inclined cylinders at the surface of the resin, said three-dimensional surface of resin thus formed was covered with an anti-fouling material (trimethylchlorosilane or TMCS).

The three-dimensional surface thus formed was then used to produce a silicone (PDMS) "countermold" so as to create negative copies of the molds. For this, a layer of a mixture of PDMS/crosslinking agent (RTV615A, General Electric, crosslinking at 70° for 1 h) is poured onto the anti-fouling treated resin surface (FIG. 4(G)). Once crosslinked, the layer of PDMS is detached from the three-dimensional surface, thus forming a negative mold of said surface (FIG. 4(H)).

Figure 5:
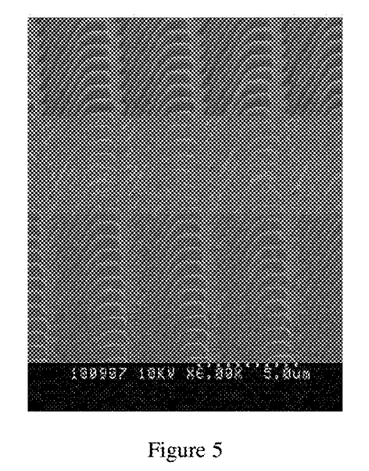
FIG. 5 presents an optical microscopy photograph of a textured surface according to the invention.

Finally, the network of inclined cylinders according to the invention is obtained by casting a mixture of PDMS/crosslinking agent (RTV615A, General Electric, crosslinking at 70° for 1 h) onto the mold after having placed the mold under vacuum for 1 h (FIG. 5).

The silicone surface is, moreover, supported by wide pillars 5 µm high and 400 µm in diameter, placed every millimeter and molded in PDMS.

Figure 1:
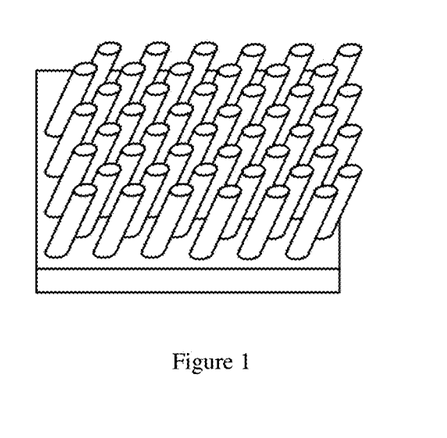
FIG. 1 illustrates a textured surface comprising a network of inclined projections of cylindrical shape.
Figure 2:
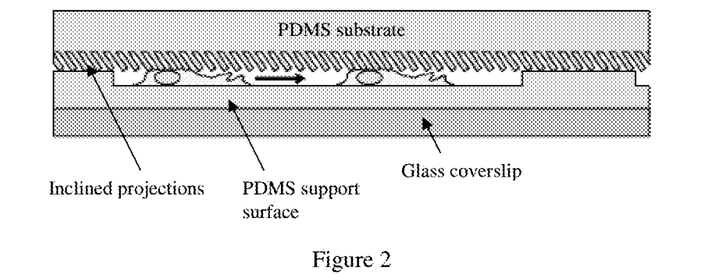
FIG. 2 illustrates the confinement of the cells between the textured surface and the support surface.
Figure 3:
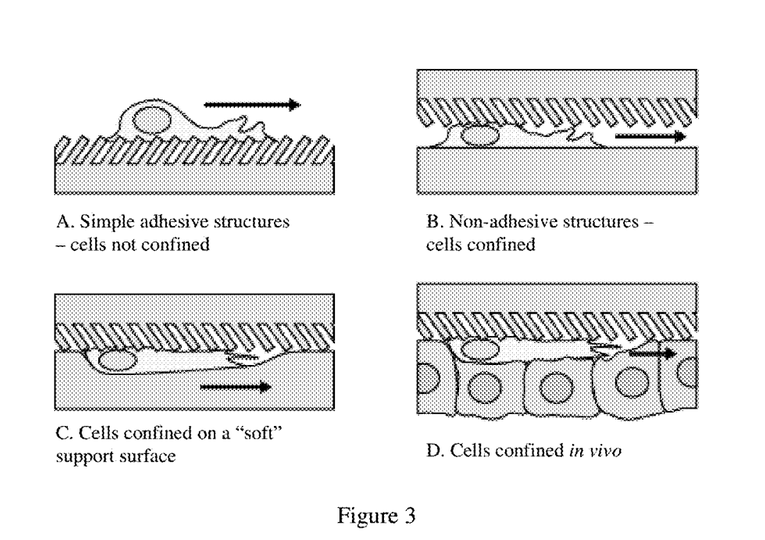
FIG. 3 illustrates various uses of the device according to the invention.

The cells in culture are therefore in contact with the inclined cylinders, without being completely crushed by them, having a space of 5 µm between the 2 surfaces in order to migrate in a confined manner (FIG. 2).

The silicone surface covered with the network of inclined cylinders is made non-adhesive by means of a chemical treatment of grafting a copolymer of poly(L-lysine) and polyethylene glycol (PLL-g-PEG).

The cell (NHDF) culture substrate, for its part, also consists of PDMS, treated with fibronectin (50 µg/ml).

Figure 6:
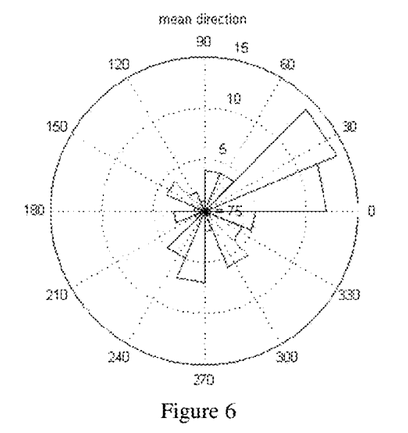
FIG. 6 represents a histogram of the mean direction of cell migration for 24 h.

Surprisingly, it was observed that the NHDFs migrate under the surface covered with inclined cylinders preferentially in the direction of inclination of the cylinders. FIG. 6 represents a histogram of the mean direction of migration of the cells for 24 h. Each element of the set represented indicates the mean direction of a cell over a period of time of 24 h after confinement. 75 cells are represented here.

This effect was also observed for various networks of projections having a diameter of 1.5 µm, and the following heights h, distances d between the projections, and angles of inclination α relative to the normal:

(h,d,a)=(7 µm, 4 µm, 80°),
(h,d,a)=(7.5 µm, 7 µm, 60°)
(h,d,a)=(5 µm, 5 µm, 45°)
(h,d,a)=(7 µm, 4 µm, 80°)
(h,d,a)=(4 µm, 4 µm, 60°)
(h,d,a)=(4 µm, 6.5 µm, 60°)
(h,d,a)=(4 µm, 9 µm, 60°) and
(h,d,a)=(4 µm, 11.5 µm, 60°)

the projections being made of various materials (PDMS, poly(lactic-co-glycolic acid) PLGA).

The invention claimed is:

1. A method for guiding cell migration, comprising bringing the cells into contact with a substrate having a textured surface which has an anisotropic three-dimensional structure, said structure consisting of a network of projections inclined relative to the normal to the plane formed by said textured surface, in the direction imparted by said anisotropic structure, said projections having a regular spacing which is smaller than the diameter of the cells, wherein the cells are conveyed on a support surface, and wherein said support surface and/or said textured surface comprises one or more additional protuberances which make it possible to control the distance between the two said surfaces.

2. The guiding method as claimed in claim 1, wherein the support surface is an artificial surface or a surface of the natural environment of said cells.

3. The guiding method as claimed in claim 1, wherein the cells are confined between said support surface and said textured surface.

4. The method as claimed in claim 1, wherein the distance between said support surface and said textured surface is between 0 and 10 µm.

5. The guiding method as claimed in claim 1, wherein the additional protuberances are in the form of pillars with a diameter of between 100 and 500 µm, and a height of less than 10 µm.

6. The guiding method as claimed in claim 2, wherein the artificial surface is selected from the group consisting of a gel cell culture surface, a glass coverslip, and the inside of a microfluidic channel.

7. The guiding method as claimed in claim 2, wherein the surface of the natural environment of said cells is selected from the group consisting of the surface of a living tissue and the surface of a wound.

8. The method as claimed in claim 1, wherein the distance between said support surface and said textured surface is between 3 and 6 µm.

9. The method as claimed in claim 5, wherein the pillars have a height of between 3 and 6 µm.

10. The method as claimed in claim 1, wherein said network of projections has a spacing which is less than 20 µm.

11. The method as claimed in claim 1, wherein said network of projections has a spacing between 0.1 and 15 µm.

12. The method as claimed in claim 1, wherein said network of projections has a spacing between 5 and 10 µm.

13. The method as claimed in claim 1, wherein said network of projections has a spacing of about 5 µm.

14. The method as claimed in claim 1, wherein the inclined projections have an angle of inclination of less than or equal to 45° relative to the normal to the plane formed by said textured surface.

15. The method as claimed in claim 1, wherein the inclined projections have an angle of inclination of between 10° and 45° relative to the normal to the plane formed by said textured surface.

16. The method as claimed in claim 1, wherein the inclined projections have an aspect ratio, corresponding to the ratio of the height to the diameter of the projections, of between 0.5 and 20.

17. The method as claimed in claim 1, wherein the inclined projections have an aspect ratio, corresponding to the ratio of the height to the diameter of the projections of between 2 and 10.

18. The method as claimed in claim 1, wherein the inclined projections are in the shape selected from the group consisting of cylinders having a spherical or ovoid cross section, cones, pyramids, lamellae having a cross section shape selected from a rectangle and a parallelogram, and flakes having a substantially triangular, semielliptical or semicircular shape.

19. The method as claimed in claim 1, wherein the inclined projections are in the shape of cylinders with a diameter of between 10 nm and 10 µm.

20. The method as claimed in claim 19 wherein the cylinders have a diameter of between 0.5 and 3 µm.

21. The method as claimed in claim 1, wherein the substrate having a textured surface is adhesive for cells.

22. The method as claimed in claim 1, wherein the substrate having a textured surface is non-adhesive for cells.

23. The method as claimed in claim 22, wherein the non-adhesive substrate consists of a non-adhesive material selected from the group consisting of a fluoropolymer and a material made non-adhesive by chemical treatment through the grafting of molecules of polyethylene glycol (PEG).

24. The method as claimed in claim 1, wherein the substrate comprises a dressing, an implant, a prosthesis, an artificial-tissue support, a microfluidic channel, or a Lab-on-a-chip device integrating channels.

25. The method as claimed in claim 24 wherein said substrate comprises a dressing.

* * * * *